United States Patent
Calhoun

(10) Patent No.: US 6,167,764 B1
(45) Date of Patent: Jan. 2, 2001

(54) STUD TENSIONING METHOD

(75) Inventor: Gregory L. Calhoun, North Huntingdon, PA (US)

(73) Assignee: Westinghouse Electric Company LLC, Pittsburgh, PA (US)

( * ) Notice: Under 35 U.S.C. 154(b), the term of this patent shall be extended for 0 days.

(21) Appl. No.: 09/339,459

(22) Filed: Jun. 24, 1999

Related U.S. Application Data

(60) Provisional application No. 60/094,474, filed on Jul. 28, 1998.

(51) Int. Cl.$^7$ .......................................... G01N 3/08
(52) U.S. Cl. ................................................ 73/837
(58) Field of Search ........................... 73/826, 831, 837, 73/840, 856, 857

(56) References Cited

U.S. PATENT DOCUMENTS

| | | |
|---|---|---|
| 3,851,906 | 12/1974 | Frisch et al. . |
| 3,994,158 * | 11/1976 | Weinhold ................... 73/798 |
| 4,047,456 | 9/1977 | Scholz . |
| 4,333,351 | 6/1982 | Bickford . |
| 4,454,790 | 6/1984 | Rieben . |
| 4,513,497 | 4/1985 | Finch . |
| 4,548,103 | 10/1985 | Orban . |
| 4,552,038 | 11/1985 | Heiermann . |
| 4,676,109 | 6/1987 | Wallace . |
| 4,686,859 | 8/1987 | Wallace . |
| 5,005,424 * | 4/1991 | Markowski ................... 73/834 |
| 5,408,509 | 4/1995 | Ruzga et al. . |
| 5,515,294 * | 5/1996 | Mohr et al. ................... 702/113 |
| 5,589,640 | 12/1996 | Butler . |

* cited by examiner

Primary Examiner—Max Noori

(57) ABSTRACT

The tension in a stud is verified by determining the elongation of the stud while attached to a stud tensioner during the tensioning step. The pressure of hydraulic fluid in a hydraulically actuated tensioner is increased from a first low pressure to a higher pressure for elongating the stud while correlating the increase in pressure of the hydraulic fluid with the quantity of hydraulic fluid in the tensioner or with the displacement of a tensioner puller bar or piston. After a nut is tightened on the stud, the pressure of the hydraulic fluid is reduced from the higher pressure to a second low pressure while correlating the decrease in pressure of the hydraulic fluid with the travel of the puller bar or piston or correlating the decrease in pressure of the hydraulic fluid with the change in fluid volume. The elongation of the stud is then determined as a function of the difference in the correlated quantities of hydraulic fluid or the correlated differences in puller bar or piston travel at the first and second low pressures. Finally, the tensioner is detached from the stud.

7 Claims, 2 Drawing Sheets

STUD TENSIONING METHOD

CROSS-REFERENCE TO RELATED APPLICATIONS

This applications claims the benefit of U.S. Provisional Application Serial Number 60/094,474 filed on Jul. 28, 1998.

BACKGROUND OF THE INVENTION

The invention relates to a stud tensioning method and more particularly to a method for determining the elongation of a stud in order to verify the load on the stud.

Removable closure heads of large vessels of the type employed to contain fuel rod assemblies in commercial nuclear power plants for generating electric power have large circumferential flanges which are secured to mating circumferential flanges on the vessels by nuts rotatably engaged with threaded studs extending upwardly from the vessel flanges and through aligned stud holes in the head flanges. As is disclosed by U.S. Pat. No. 3,851,906 to Frisch et al., there may be up to 54 such studs or more and the studs may have diameters of about 7 inches. The nuts may be as long as about 6 inches or more.

These heads are removed every one to two years during scheduled refueling outages to replace spent fuel rod assemblies with fresh fuel rod assemblies and to shuffle the still useful fuel rod assemblies in the reactor vessel. About a third of the fuel rod assemblies are replaced during these outages. Once the fuel rod assemblies have been reloaded and shuffled, the closure heads are replaced on the flanges and secured to the reactor vessels by tightening the nuts with commercially available tensioners to load the studs extending through the flanges of the heads to the extent that the studs are elastically stretched. All of these refueling and associated activities are performed on critical path schedules and involve daily costs of hundreds of thousands of dollars or more for every day the plant is in the outage and not generating electric power in addition to the cost of performing the refueling. Accordingly, it is highly desirable to rapidly perform these activities.

The Frisch et al. Patent discloses a stud tensioning method for securing the studs on the heads of nuclear reactor vessels which is generally employed today. According to the Frisch et al. Patent, one or more stud tensioners are employed to tighten the nuts on the studs. Measurement of the elongation of each stud is employed to verify that the stud has been properly tightened. The elongation measurements are intended to minimize uncertainties due to variations in residual loads on the studs caused by variations in the actual pressure applied to the studs by the tensioner, high friction in the stud threads and possibly operator error. The elongation of each stud is determined by measuring the length of the stud with a measuring rod inserted in an axially extending bore in the stud before and then after the tensioning step. The elongation of the stud is determined by the difference in the measured lengths. These measurements normally are performed in series with the tensioning step because the measuring rods are normally removed to protect them from being bent by the large, heavy, suspended tensioners as they are manipulated around the studs by the operators.

Because the measurements are performed in series with the tensioning step, the measurement times for up to 54 studs or more can require up to about two and one half hours if no serious discrepancies develop. However, if a discrepancy is found, the tensioning and elongation measurements must be repeated until the measurements satisfy the specifications, which can add hours to the critical path schedules.

Other tightening techniques may be employed, but they may be subject to small but unacceptable inaccuracies. Thus, the nuts may be torqued to a predetermined setpoint, but friction in the threads may result in a lower tensioning force being transmitted to the studs. Nut rotations may be determined in other practices, but the initial points may not always be determined with sufficient accuracy.

SUMMARY OF THE INVENTION

It is an object of the present invention to provide a stud tensioning method which measures the elongation of the stud contemporaneously with the stud tensioning step rather than serially. It is a further object to provide a method which accurately measures elongation.

With these objects in view, the present invention resides in a method of determining the elongation of a tensioned stud. A hydraulically actuated tensioner is attached to a stud extending from a body. The pressure of the hydraulic fluid of the tensioner is increased from a first low pressure to a higher pressure for elongating the stud while correlating the increase in pressure of the hydraulic fluid either with the volume of hydraulic fluid in at least a portion of the tensioner or with the displacement of a tensioner member for at least a portion of the pressure increase. The nut is tightened on the stud. The pressure of the hydraulic fluid is reduced from the higher pressure to a second low pressure while correlating the decrease in pressure of the hydraulic fluid either with the volume of hydraulic fluid in the tensioner or with the displacement of the tensioner member. The elongation of the stud is then determined as a function of either the difference in the correlated volumes of hydraulic fluid or the correlated differences in displacement of the tensioner member at the first and second low pressures. Finally, the tensioner is detached from the stud.

BRIEF DESCRIPTION OF THE DRAWINGS

The invention as set forth in the claims will become more apparent from the following detailed description of a preferred practice thereof shown, by way of example only, in the accompanying drawings, wherein:

DESCRIPTION OF THE PREFERRED PRACTICE

Figure 1:
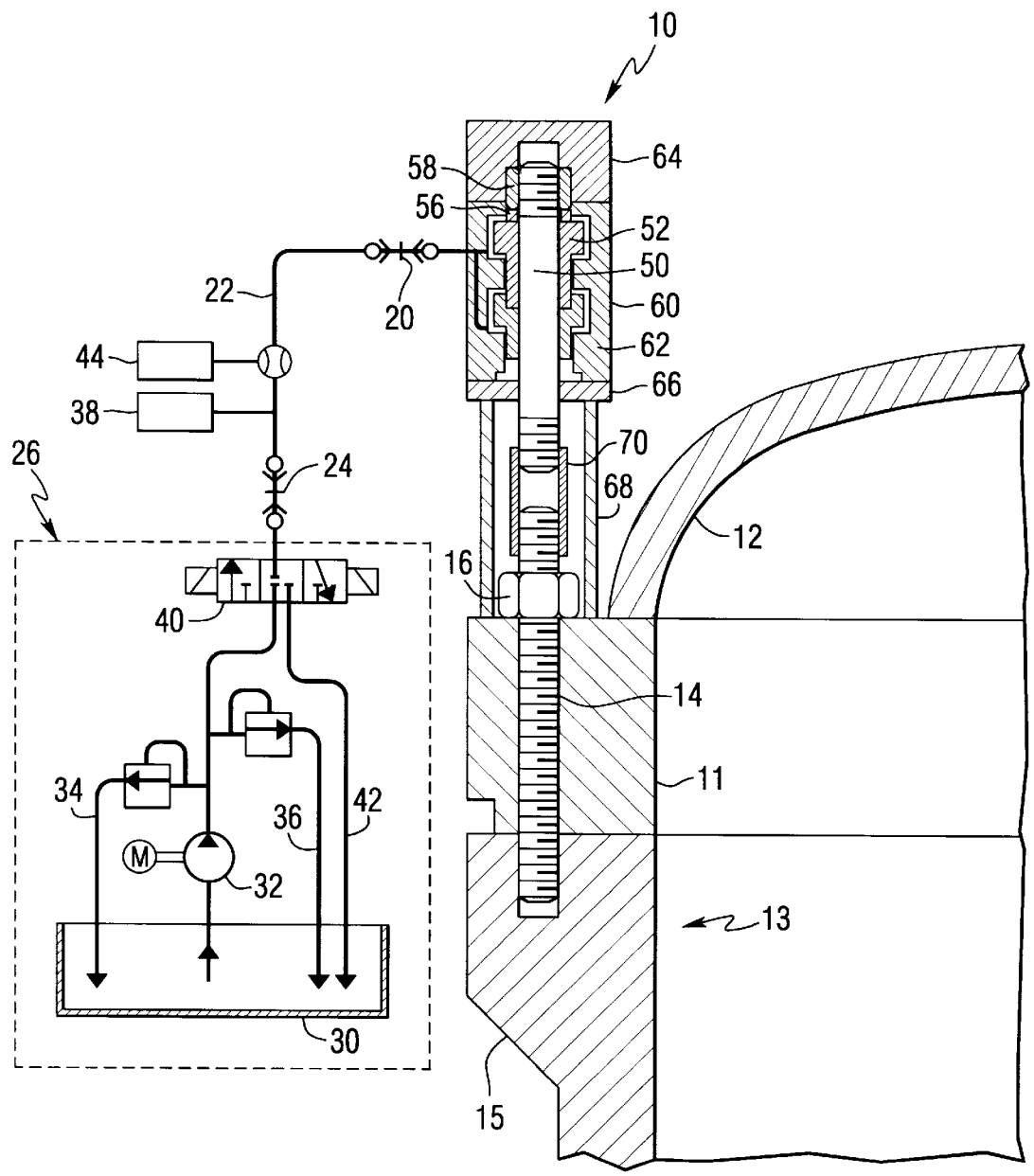
FIG. 1 is a schematic representation of a hydraulically actuated tensioner attached to a stud of a vessel which may be employed in the practice of the present invention.

Referring now to the drawings in detail and in particular to FIG. 1 there is shown a hydraulically actuated tensioner 10 resting on a circumferential flange 11 of a removable head 12 of a body illustrated by vessel 13. A plurality of studs, illustrated by stud 14, may extend upwardly from a vessel flange 15, through the head flange 11 and threadedly engage nuts illustrated by nut 16. In the intended commercial practice of the present invention, the vessel 13 is a reactor vessel containing nuclear fuel rods in a commercial pressurized water nuclear power plant for generating electricity. Such reactor vessels 13 have diameters of up to 12 feet or more and are designed to operate at pressures of up to 2500 psi or more and at temperatures of up to 650° F. or more. A reactor vessel 13 may have up to 54 studs 14 weighing up to about 600 pounds each and having diameters of about 7 inches and the nuts 16 may be 6 inches long. FIG. 1 illustrates a condition where the vessel 13 has been closed, the head 12 replaced and the nut 16 is being tightened by the hydraulically actuated tensioner 10 to secure the head 12 to the vessel 13 before returning to power generating operations. In an actual situation, there may be three or more tensioners 10 operated simultaneously by three or more people. Six tensioners 10 are frequently employed.

The tensioner 10 is connected through fittings 20 and a hydraulic line 22 to fittings 24 of a remotely located hydraulic tensioning unit 26. Any suitable commercially available tensioning unit 26 may be employed. The tensioning unit 26 generally includes a reservoir 30 for retaining oil or another suitable hydraulic liquid, a pump 32, pressure relief lines 34 and 36, a shutoff valve 40 and a by-pass line 42. In addition, a pressure indicator 38 and a flow meter 44 may be employed in hydraulic line 22. In applications where the tensioning unit 26 is employed to control two or more tensioners 10 simultaneously, one pressure indicator 38 may be employed in a manifold from the unit 26 to determine the pressure in the system and separate hydraulic lines 22 each with an in-line flow meter 44 may be connected between the manifold and the tensioner 10 (not shown). A computer controlled hydraulic tensioning unit 26 may be used.

As shown in FIG. 1, the tensioner 10 itself generally has a puller bar 50 (or actuator shaft) fastened to a single or multiple stage piston 52. The piston 52 acts against a washer 56 and a fixed nut 58, all of which are disposed in a cylinder 60 defined by a housing 62 extending between a top plate 64 and a bottom plate 66. A cylindrical base 68 extending from the bottom plate 66 supports the tensioner 10 on the head flange 11. A gripper nut 70 (or other connector) extends from the puller bar 50 to grip the top of the stud 14.

To elastically stretch the stud 14, the pump 32 pumps hydraulic fluid through hydraulic line 22 to the piston cylinder 60 and increases the pressure of the hydraulic fluid in the cylinder 60 up to a pressure setpoint which may be up to about 7000 psi or more to move the piston 52, puller bar 50 and gripper 70 upwardly. In addition to the stud 14, the puller bar 50 and gripper nut 70 are stretched elastically in the process (each article being stretched in accordance with the relationship: applied force upon an article is equal to the spring constant of the article multiplied by the elongation of the article). The upwardly acting hydraulic force also acts against the weight of the piston 52 and commonly against low pressure (about 90 psi) air which may be continuously applied to the top of the piston 52 to assist in later returning the piston 52 to its zero position and the end of the tensioning step. After tightening the nut 16, the hydraulic system is vented and the hydraulic pressure and tension applied to the stud by the gripper 70 are relieved in about two seconds or more time. The structure and operation of similar stud tensioners are disclosed in more detail by U.S. Pat. Nos. 4,844,418; 4,552,038; 4,223,575; 4,047,456 and 3,851,906, which are incorporated by this reference for these disclosures.

In the practice of the present invention, the elongation measurements may be taken during the tensioning process while the tensioner 10 is operatively connected with the studs 14. Incremental measurements may be made and corrective action taken (if necessary) before detaching the tensioner 10 with less impact on the critical path compared with the prior art practice. Stud elongation may be determined by measuring the travel of a tensioner member such as the puller bar 50 or the piston 52 in cylinder 60 and correlating piston or puller bar travel (or, equivalently, the change in volume of hydraulic liquid in the piston cylinder) with the pressure in the hydraulic system. Initially, and prior to actual stud tensioning, there is so-called free piston or puller bar travel (indicated by exemplary points 80–82 on FIG. 2; and 80'–82' on FIG. 3) reflecting the mechanical clearance of the nut 16, which does not contribute to elongation of the stud. During tensioning (indicated by exemplary points 82–84 and 84–86 on FIG. 2; and 82'–84' and 84'–86' on FIG. 3), the piston 52 or puller bar 50 travel is substantially directly proportional to the change in the hydraulic pressure.

Figure 2:
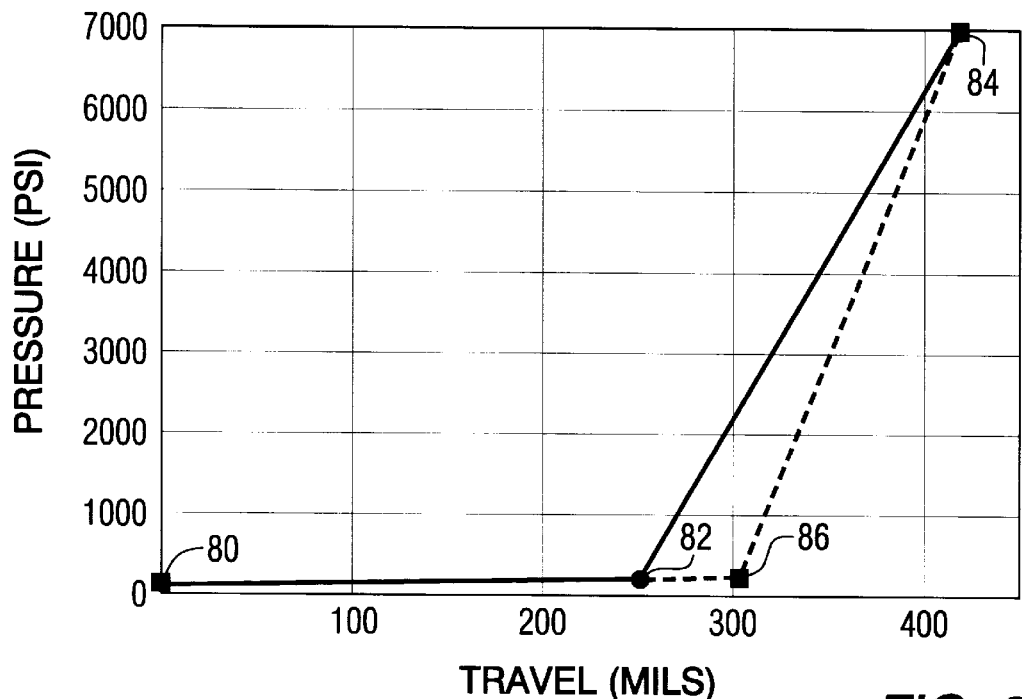
FIG. 2 is a graph correlating hydraulic pressure of a tensioner with the displacement of a tensioner piston.

FIG. 2 shows an exemplary correlation between piston 52 (or, equivalently, puller bar 50) travel, hydraulic pressure and stud elongation as determined during a test on a 7 inch diameter stud with a Biach Model 2-5067-2 tensioner. As the system pressure increased from its zero point corresponding to point 80 to a first low pressure corresponding to point 82, the piston 52 traveled from an initial position at a relatively low, substantially constant rate to an intermediate position (which travel reflects free travel) and then the pressure increased at a substantially increased, substantially constant rate (which travel reflects tensioning). As the pressure increased to a setpoint pressure of 7000 psi as is shown on FIG. 2, the piston 52 traveled to a final position as indicated at point 84. (In addition to stretching the stud 14, the puller bar 50 and gripper nut 70 generally stretch as well, but prior calibration of the tensioning unit 26 compensated for such additional effects.) This setpoint pressure may be an intermediate pressure or the final pressure of the specification. At this point the nut 16 may be tightened in accordance with specified procedures.

The hydraulic pressure is then relieved to a second low pressure and the piston will travel to an intermediate position 86. It is noted that the return piston 52 travel is not reflected by line 84-82 because the weight of the piston 52 and the 90 psi backpressure on the piston 52 now aid downward piston displacement so that there is relatively greater displacement associated with a given change in the system pressure. In the ideal case where there is relatively low friction in the piston seals, the second low pressure will be substantially the same as the first low pressure and the changes in slope of operating lines 80-82-84 and 84-86-80 will be sharply indicated as shown. Because there may be uncertainty in determining the second low pressure (principally because of friction in the piston seals), the second low pressure (corresponding to position 86) may be different from the first low pressure. Thus, e.g., the second low pressure may be preselected at about 200 psig or less. Continued reduction in the hydraulic pressure will result in piston travel back to the initial position 80 substantially along line 86-80.

The elongation of the stud 14 then is equivalent to the distance between points 82 and 86. Thus, FIG. 2 indicates that the elongation of the stud 14 was about 50 mils (300 mils less 250 mils). FIG. 2 also indicates that the free travel was about 250 mils.

Figure 3:
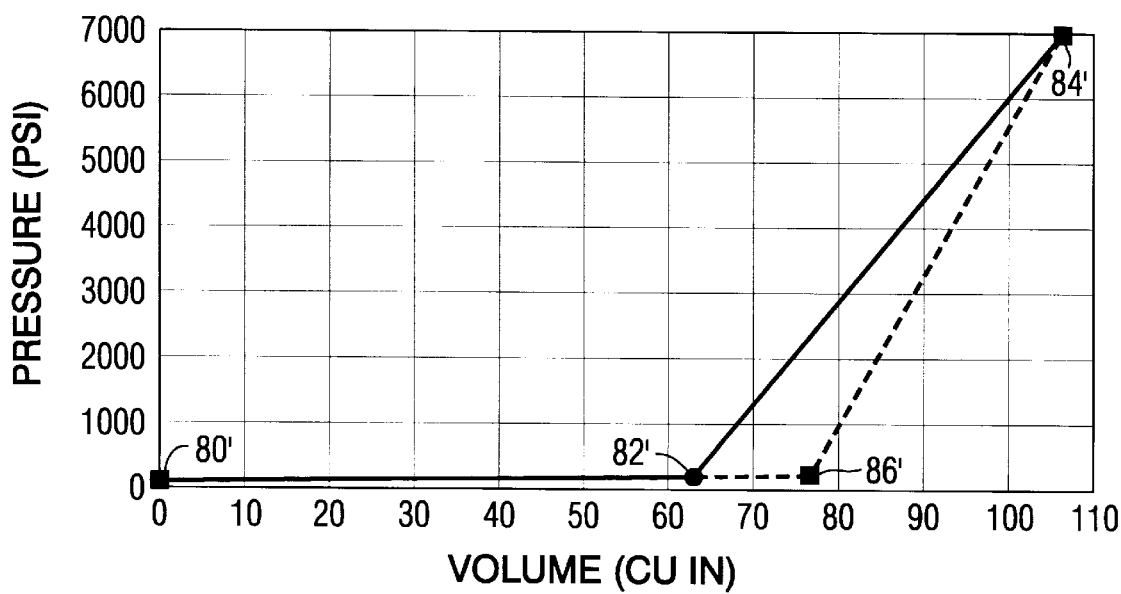
FIG. 3 is a graph correlating the hydraulic pressure of a tensioner with the displaced volume of the tensioner piston of FIG. 2.

In lieu of direct measurement of the movement of a tensioner member such as piston or puller bar travel, a flow meter 44 may be alternatively employed to measure the volume of liquid pumped into the tensioner 10. The liquid flow may then be correlated with the hydraulic pressure as shown in FIG. 3, which shows equivalent points described in FIG. 2 but identified with primed numerals. Flow measurements will be dependent upon the condition of the piston seals and, therefore, may not be as accurate as linear displacement measurements. Thus, for example, flow meters are generally accurate to within 1 mil to 5 mils whereas puller bar or piston displacement generally may be accurately determined to within 1 mil. As an alternative, the accuracy of flow measurements may be improved to within 1 mil to 2 mils by extrapolating a best fit line 84'-86' from data points taken near the setpoint pressure (by, e.g., a data acquisition device operatively associated with a controlling computer) down to a preselected lower pressure of about 200 psi, determining the displacement based upon the extrapolated point (i.e., point 84'). Thus, either piston travel or displaced liquid volume may be measured to indicate stud elongation. By setting limits on these measures, incremental elongations can be verified in process and corrections can be made immediately if required. Also, the need for metering rods, dial indicators and stud length measurements before and after tensioning can be eliminated. Further the need for correction passes may be reduced or eliminated.

The relationship between hydraulic pressure and either puller bar 50 or piston 52,54 travel or displaced liquid volume may be used electronically to provide for process control or monitoring of incremental stud elongation during tensioning. Signals derived from a pressure indicator 38 in the hydraulic supply line and either a flow meter 44 in the individual tensioner's 10 supply line 22 or a displacement transducer indicating tensioner piston travel can be processed to produce the correlation shown in FIGS. 2 and 3.

While a present preferred embodiment of the present invention has been shown and described, it is to be understood that the invention may be otherwise variously embodied within the scope of the following claims of invention.

What is claimed is:

1. A method of determining the elongation of a tensioned stud, comprising the steps of:
   attaching a hydraulically actuated tensioner to a stud extending from a body;
   increasing the pressure of the hydraulic fluid of the tensioner from a first low pressure to a higher pressure for elongating the stud while correlating the increase in pressure of the hydraulic fluid either with the volume of hydraulic fluid in at least a portion of the tensioner or with the displacement of a tensioner member for at least a portion of the pressure increase;
   tightening a nut on the stud;
   reducing the pressure of the hydraulic fluid from the higher pressure to a second low pressure while correlating the decrease in pressure of the hydraulic fluid either with the volume of hydraulic fluid in at least the portion of the tensioner or with the displacement of at least the portion of the tensioner member;
   determining the elongation of the stud as a function of either the difference in the correlated volumes of hydraulic fluid or the correlated differences in displacement of the tensioner member at the first and second low pressures; and then detaching the tensioner from the stud.

2. The method of claim 1, wherein the determination of elongation of the stud includes the step of: correcting for free travel of the tensioner member.

3. The method of claim 1, wherein the elongation of the stud is determined by measuring the displacement of a piston.

4. The method of claim 1, wherein the elongation of the stud is determined by measuring the displacement of a puller bar.

5. The method of claim 1, wherein the elongation of the stud is measured by correlating the change in volume of the hydraulic fluid with the change in hydraulic pressure.

6. The method of claim 5, wherein the volume of the hydraulic fluid at the second lower pressure is calculated by extrapolating the relationship of fluid volume and system pressure observed at higher system pressures.

7. The method of claim 6, wherein the relationship of fluid volume and system pressure observed at system pressures of from about 4000 psi to about 7000 psi is extrapolated to determine the relationship of fluid volume at a system pressure of below about 200 psi.

* * * * *